(12) United States Patent
Xie et al.

(10) Patent No.: US 12,618,773 B2
(45) Date of Patent: May 5, 2026

(54) SPECTROMETER FOR DETECTING TRACE ELEMENT IN AGRICULTURAL PRODUCT AND USE THEREOF

(71) Applicants:ZHEJIANG UNIVERSITY, Hangzhou (CN); ZHEJIANG KEPLER TECHNOLOGY CO., LTD., Jiaxing (CN)

(72) Inventors: Lijuan Xie, Hangzhou (CN); Yingjie Zheng, Hangzhou (CN); Yibin Ying, Hangzhou (CN); Lin Li, Hangzhou (CN)

(73) Assignees: ZHEJIANG UNIVERSITY, Hangzhou (CN); ZHEJIANG KEPLER TECHNOLOGY CO., LTD., Jiaxing (CN)

( * ) Notice: Subject to any disclaimer, the term of this patent is extended or adjusted under 35 U.S.C. 154(b) by 204 days.

(21) Appl. No.: 18/613,198

(22) Filed: Mar. 22, 2024

(65) Prior Publication Data

US 2024/0230527 A1 Jul. 11, 2024

Related U.S. Application Data

(63) Continuation of application No. PCT/CN2023/096349, filed on May 25, 2023.

(30) Foreign Application Priority Data

Jun. 15, 2022 (CN) ........................ 202210675317.X

(51) Int. Cl.
G01N 21/35 (2014.01)
G01N 21/3563 (2014.01)
G01N 33/02 (2006.01)

(52) U.S. Cl.
CPC ....... *G01N 21/3563* (2013.01); *G01N 33/025* (2013.01); *G01N 2201/061* (2013.01)

(58) Field of Classification Search
CPC ............ G01N 21/3563; G01N 33/025; G01N 2201/061
See application file for complete search history.

(56) References Cited

U.S. PATENT DOCUMENTS 5,867,265 A 2/1999 Thomas
2004/0065829 A1* 4/2004 Burk ...................... G01N 21/86
359/236

(Continued)

FOREIGN PATENT DOCUMENTS

CN 106323909 A 1/2017
CN 207675640 U 7/2018

(Continued)

*Primary Examiner* — Hugh Maupin
(74) *Attorney, Agent, or Firm* — Bayramoglu Law Offices LLC

(57) ABSTRACT

A spectrometer for detecting a trace element in an agricultural product and use thereof is provided. The spectrometer includes: a light source device configured to generate light required by spectroscopic detection; a convergence device configured to converge the light generated by the light source device; a chopping device configured to modulate a frequency of light converged by a convergence device; a filter device configured to shield light of a wavelength other than a preset wavelength; a detection device configured to receive light passing through a to-be-detected agricultural product and the filter device, and convert an optical signal into an electrical signal; and a processing device configured to generate spectroscopic analysis data according to the electrical signal outputted by the detection device and output a substance content analysis result according to the spectroscopic analysis data, where the preset wavelength of the filter device ranges from 400 nm to 5,000 nm.

18 Claims, 6 Drawing Sheets

(56)                    References Cited

U.S. PATENT DOCUMENTS

| | | | | |
|---|---|---|---|---|
| 2004/0130714 A1* | 7/2004 | Gellerman | ................ | G01J 3/44 |
| | | | | 356/300 |
| 2004/0248285 A1* | 12/2004 | Casey | ............... | G01N 21/6486 |
| | | | | 435/287.2 |
| 2005/0213192 A1* | 9/2005 | Murtagh | ................ | G01J 3/433 |
| | | | | 359/298 |
| 2008/0030718 A1 | 2/2008 | Tamai et al. | | |
| 2010/0284005 A1* | 11/2010 | Malinen | ................... | G01J 3/02 |
| | | | | 356/326 |
| 2014/0291480 A1* | 10/2014 | Bruder | ................... | G01S 17/89 |
| | | | | 250/206 |
| 2015/0285685 A1* | 10/2015 | Wax | .................. | G01B 9/02091 |
| | | | | 356/456 |
| 2020/0041410 A1* | 2/2020 | Ashrafi | ................. | G01N 21/59 |
| 2022/0221338 A1* | 7/2022 | Rodriguez-Saona | ..... | G01J 3/44 |
| 2022/0333993 A1* | 10/2022 | Valouch | ............... | G01J 3/0232 |
| 2023/0266234 A1* | 8/2023 | Oeguen | ............... | G01J 3/0256 |
| | | | | 356/326 |
| 2025/0198840 A1* | 6/2025 | Ilovitsh | ................. | G02B 26/04 |
| 2025/0224332 A1* | 7/2025 | Oeguen | ............... | G01N 21/359 |

FOREIGN PATENT DOCUMENTS

| | | |
|---|---|---|
| CN | 114324195 A | 4/2022 |
| CN | 115219448 A | 10/2022 |
| KR | 20000074001 A | 12/2000 |

* cited by examiner

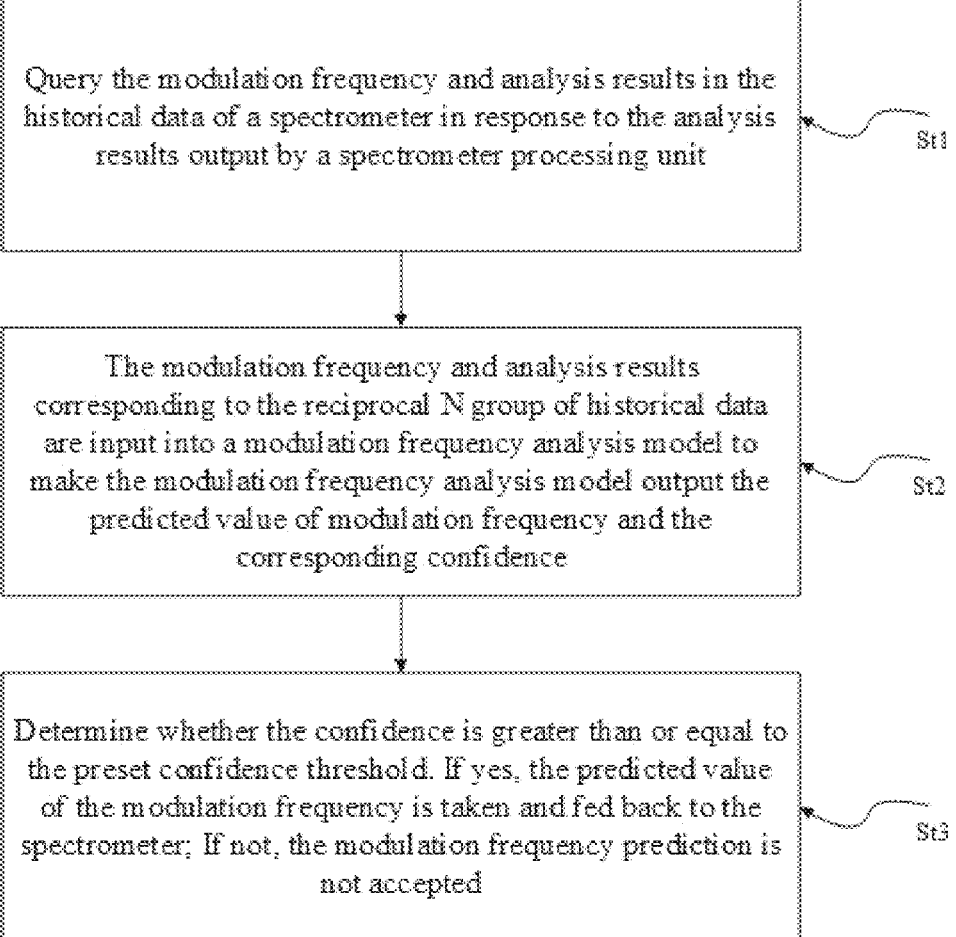

Query the modulation frequency and analysis results in the historical data of a spectrometer in response to the analysis results output by a spectrometer processing unit — St1

The modulation frequency and analysis results corresponding to the reciprocal N group of historical data are input into a modulation frequency analysis model to make the modulation frequency analysis model output the predicted value of modulation frequency and the corresponding confidence — St2

Determine whether the confidence is greater than or equal to the preset confidence threshold. If yes, the predicted value of the modulation frequency is taken and fed back to the spectrometer; If not, the modulation frequency prediction is not accepted — St3

FIG. 4

SPECTROMETER FOR DETECTING TRACE ELEMENT IN AGRICULTURAL PRODUCT AND USE THEREOF

CROSS REFERENCE TO THE RELATED APPLICATIONS

This application is the continuation application of International Application No. PCT/CN2023/096349, filed on May 25, 2023, which is based upon and claims priority to Chinese Patent Application 202210675317.X, filed on Jun. 15, 2022, the entire contents of which are incorporated herein by reference.

TECHNICAL FIELD

The present disclosure relates to the technical field of nondestructive detection on agricultural products, and in particular to a spectrometer for detecting a trace element in an agricultural product and use thereof.

BACKGROUND

Quality classification of agricultural products, particularly fruits, has become an additional condition in cross-border trade and an important method to improve the added value. For agricultural products, there are mainly external quality (including size, shape, color, and surface defect) and internal quality (including sugar content, sourness, and ripeness).

Infrared spectroscopy is considered as a powerful tool to determine a molecular composition and a molecular structure. A near-infrared light region mainly includes an absorption band generated by absorption of a doubled frequency and a combined frequency in stretching vibration of hydrogen-containing groups (such as O—H, N—H, and C—H). Benefiting from near-infrared spectroscopy (NIRS), nondestructive detection of the internal quality of agricultural products has become possible. Nowadays, detection of the internal quality of some high-benefit agricultural products can be achievable. For example, sugar content and sourness of the fruit can be detected and taken as a classification basis to classify the internal quality of the fruit, thereby improving the economic benefit.

It is of great significance to use infrared spectroscopy to detect a healthy trace element (such as lycopene) in agricultural products. Lycopene is widely found in tomatoes, tomato products, watermelons, grapefruits, and other fruits. It is the main pigment in ripe tomatoes and one of the common carotenoids. Evidence shows that lycopene can effectively reduce the occurrence of tumors such as prostate cancer, cardiovascular diseases, etc. Hence, it is important to classify the lycopene content of lycopene-containing agricultural products. However, since the lycopene content in agricultural products is far lower than the content of other components, at present, the lycopene content is detected with destructive detection methods such as spectrophotometry, thin-layer chromatography, and high-performance liquid chromatography, and these methods are obviously far from satisfactory for quick classification of agricultural products. Moreover, spectroscopic data obtained by a conventional near-infrared spectrometer include little optical information associated with the lycopene content. Therefore, it is still hard to realize quick, nondestructive detection of the lycopene content in agricultural products.

SUMMARY

Concepts of the present disclosure are briefly described in summary, and these concepts will be described in detail in the following specific implementations. The present disclosure is not intended to identify key features or essential features of the protected technical solution, nor is it intended to limit the scope of the protected technical solution.

Embodiments of the present disclosure provide a spectrometer for detecting a trace element in an agricultural product and use thereof, to solve the technical problems in the background.

According to a first aspect, an embodiment of the present disclosure provides a spectrometer for detecting a trace element in an agricultural product, including: a light source device configured to generate light required by spectroscopic detection; a convergence device configured to converge the light generated by the light source device; a chopping device configured to modulate a frequency of light converged by the convergence device; a filter device configured to shield light of a wavelength other than a preset wavelength; a detection device configured to receive light passing through a to-be-detected agricultural product and the filter device, and convert an optical signal into an electrical signal; and a processing device configured to generate spectroscopic analysis data according to the electrical signal outputted by the detection device and output a substance content analysis result according to the spectroscopic analysis data, where the preset wavelength of the filter device ranges from 400 nm to 5,000 nm.

Further, the light generated by the light source device includes infrared light. Further, a wavelength of the light generated by the light source device ranges from 400 nm to 5,000 nm.

Further, the light source device includes a halogen lamp.

Further, the convergence device at least includes a convex lens.

Further, the chopping device includes: an optical chopper including a rotary vane with adjustable rotational frequency for periodically shielding the light converged by the convergence device; a chopper driver configured to drive the rotary vane to rotate; and a chopper controller configured to control operation of the chopper driver to control a rotational frequency of the rotary vane, where the chopper driver is mechanically connected to the rotary vane of the optical chopper, and the chopper driver is electrically connected to the chopper controller.

Further, the spectrometer for detecting a trace element in an agricultural product further includes: a phase lock device configured to improve a signal-to-noise ratio (SNR) of the electrical signal outputted by the detection device to the processing device.

Further, the phase lock device includes a lock-in amplifier, and the lock-in amplifier is electrically connected to the detection device, the chopper controller and the processing device, respectively.

Further, the detection device includes a near-infrared photodetector; and the near-infrared photodetector includes at least one of a Polycrystalline lead sulfide (PbS) detector array or an Indium Gallium Arsenide (InGaAs) detector array for detecting an optical signal of the preset wavelength.

Further, the spectrometer for detecting a trace element in an agricultural product further includes: a signal amplifier configured to amplify an optical signal passing through the filter device and having the preset wavelength; and the signal amplifier is made of a metamaterial having a micro-nano structure array.

According to a second aspect, an embodiment of the present disclosure provides use of the spectrometer for detecting a trace element in an agricultural product, where the spectrometer for detecting a trace element in an agricultural product is used to detect a lycopene content in an agricultural product.

The present disclosure has the following beneficial effect: The spectrometer for detecting a trace element in an agricultural product can effectively detect the substance content in the agricultural product, and its use is provided.

BRIEF DESCRIPTION OF THE DRAWINGS

The accompanying drawings constituting a part of the present disclosure are provided for further understanding of the present disclosure to make other features, objectives and advantages of the present disclosure more apparent. The schematic drawings of the present disclosure and description thereof are provided to illustrate the present disclosure and do not constitute an undue limitation to the present disclosure.

In addition, same or similar reference numerals throughout the accompanying drawings indicate same or similar elements. It should be understood that the drawings are schematic and are not drawn proportionally.

In the accompanying drawings:

FIG. 1 is a structural block diagram of a spectrometer according to an embodiment of the present disclosure;

FIG. 2 is a block diagram illustrating steps of a spectroscopic detection method according to an embodiment of the present disclosure;

FIG. 3 is a schematic diagram of a spectroscopic detection system according to an embodiment of the present disclosure;

FIG. 4 is a schematic diagram of a spectroscopic detection device according to an embodiment of the present disclosure; and FIG. 5 is a block diagram illustrating a part of steps of a spectroscopic detection method according to another embodiment of the present disclosure; and FIG. 6 is a schematic structural diagram of electronic equipment according to an embodiment of the present disclosure.

REFERENCE NUMERALS

100: spectrometer;
101: light source device, and 102: convergence device;
103: chopping device, 1031: optical chopper, 1032: chopper driver, and 1033: chopper controller;
104: filter device;
105: detection device, 1051: near-infrared photodetector, 105*a*: PbS detector array, and 105*b*: InGaAs detector array;
106: processing device;
107: phase lock device, and 1071: lock-in amplifier;
108: signal amplifier;
200: to-be-detected agricultural product; and
300: server.

DETAILED DESCRIPTION OF THE EMBODIMENTS

Embodiments of the present disclosure will be described below in more detail with reference to the accompanying drawings. Although some embodiments of the present disclosure are shown in the accompanying drawings, it should be understood that the present disclosure can be implemented in various forms and should not be construed as being limited to the embodiments illustrated herein. On the contrary, these embodiments are provided to help more thoroughly and completely understand the present disclosure. It should be understood that the accompanying drawings and the embodiments of the present disclosure are only used as examples, and are not intended to limit the protection scope of the present disclosure.

It should also be noted that, for convenience of description, only the parts related to the present disclosure are shown in the accompanying drawings. The embodiments in the present disclosure and features in the embodiments may be combined with each other in a non-conflicting manner.

It is to be noted that concepts such as "first" and "second" in the present disclosure are merely intended to distinguish different devices, modules or units, rather than limit a sequence or a mutual dependent relationship of functions executed by the device, the module or the unit.

It is to be noted that terms such as "a" and "a plurality of" in the present disclosure are schematic rather than restrictive. Unless otherwise clearly specified in a context, these terms should be understood as "one or more" to those skilled in the art.

A name of a message or information interacted between a plurality of devices in implementations of the present disclosure is merely illustrative, rather than a limit to the scope of the message or information.

The present disclosure is described in detail below with reference to the accompanying drawings and embodiments.

Figure 1:
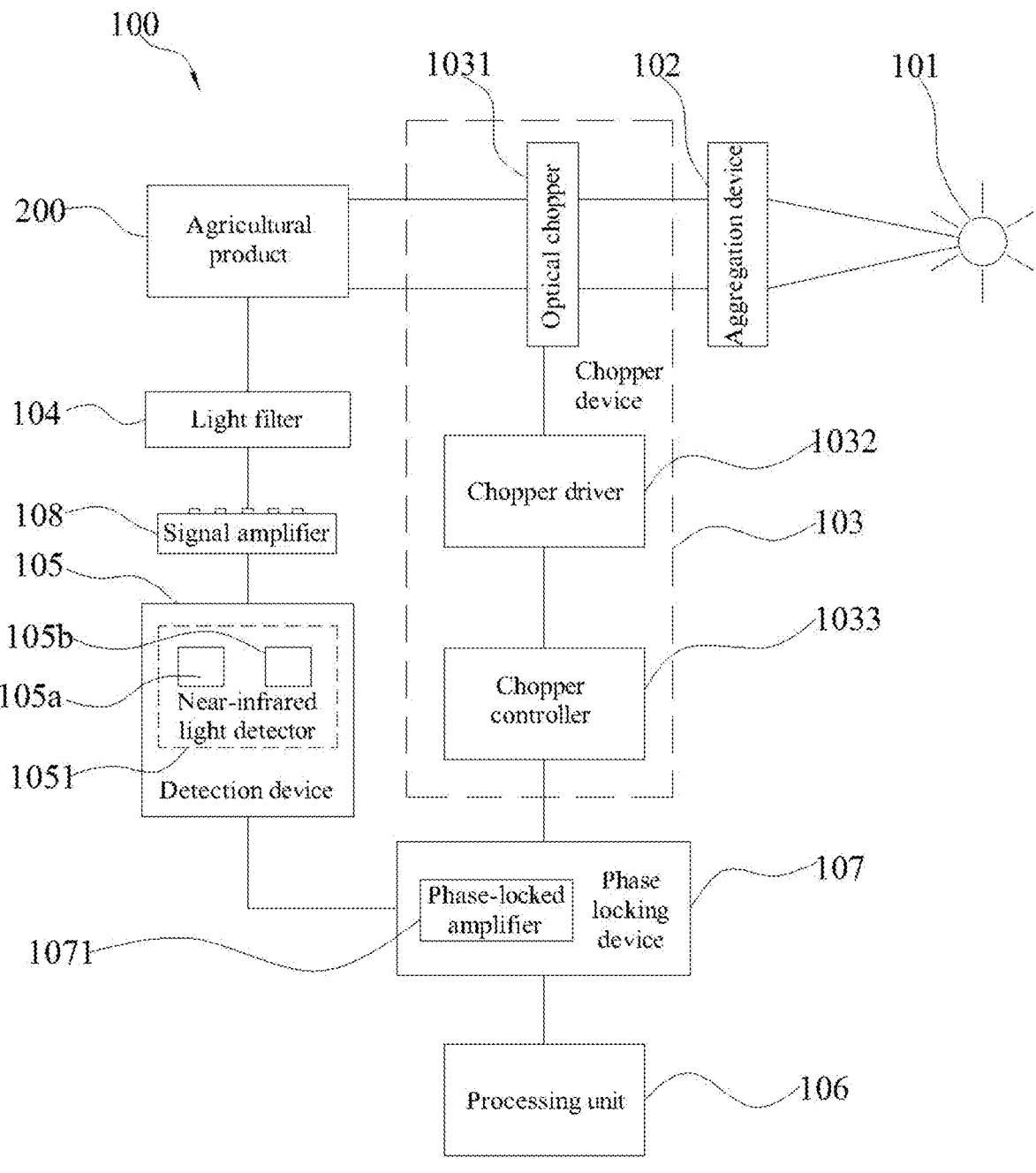

As shown in FIG. 1, an embodiment of the present disclosure provides spectrometer 100, including: light source device 101, convergence device 102, chopping device 103, filter device 104, detection device 105, and processing device 106.

The light source device 101 is configured to generate light required by spectroscopic detection. The convergence device 102 is configured to converge the light generated by the light source device 101. The chopping device 103 is configured to modulate a frequency of light converged by the convergence device. The filter device 104 is configured to shield light of a wavelength other than a preset wavelength. The detection device 105 is configured to receive light passing through to-be-detected agricultural product 200 and the filter device 104, and convert an optical signal into an electrical signal. The processing device 106 is configured to generate spectroscopic analysis data according to the electrical signal outputted by the detection device 105 and output a substance content analysis result according to the spectroscopic analysis data.

With the above solution, due to a low content of a trace substance or a nutrient substance in the agricultural product, characteristic wavelengths of some trace substances or nutrient substances (such as a characteristic wavelength associated with a chemical component of lycopene) are selected artificially in a near-infrared band in the spectrometer 100 provided by the present disclosure. This greatly reduces useless spectroscopic information in an original spectrum, and is of guiding significance to detect the trace element in the agricultural product.

Specifically, the preset wavelength of the filter device ranges from 400 nm to 5,000 nm. According to the trace substance to be detected or the nutrient substance to be detected, the preset wavelength of the filter device is set correspondingly to filter light of an uncharacteristic wavelength.

More specifically, the preset wavelength of the filter device 104 includes at least one or more of 900 nm, 1,180 nm, 1,400 nm, 1,720 nm and 2,350 nm. These preset wavelengths are used to detect the lycopene.

As a preferred solution, the filter device includes one or more filters.

Specifically, the light generated by the light source device 101 includes infrared light. A wavelength of the infrared light covers the characteristic wavelength of the trace substance or the nutrient substance. More specifically, the light source device 101 includes a halogen lamp.

More specifically, a wavelength of the light generated by the light source device 101 ranges from 400 nm to 5,000 nm.

As a specific solution, the convergence device 102 at least includes a convex lens. The convex lens is preferably a planoconvex lens. A non-convex surface of the planoconvex lens is close to the light source device.

As a specific solution, the chopping device 103 includes: optical chopper 1031, chopper driver 1032, and chopper controller 1033. The optical chopper 1031 includes a rotary vane with adjustable rotational frequency for periodically shielding the light converged by the convergence device. The chopper driver 1032 is configured to drive the rotary vane to rotate. The chopper controller 1033 is configured to control operation of the chopper driver 1032 to control a rotational frequency of the rotary vane. The chopper driver 1032 is mechanically connected to the rotary vane of the optical chopper 1031. The chopper driver 1032 is electrically connected to the chopper controller 1033.

With the above solution, the chopper controller 1033 outputs a modulated frequency electrical signal to control a modulation frequency of the optical chopper 1031 and modulate the light converged by the convergence device to a high-frequency optical signal at a preset frequency.

As a specific solution, the detection device 105 includes near-infrared photodetector 1051. The near-infrared photodetector 1051 includes at least one of a PbS detector array 105a or an InGaAs detector array 105b, so as to realize detection of the preset wavelength. As a preferred solution, the spectrometer 100 provided by the embodiment of the present disclosure further includes: phase lock device 107. The phase lock device 107 is configured to improve an SNR of the electrical signal outputted by the detection device 105 to the processing device 106. Specifically, the phase lock device 107 includes lock-in amplifier 1071. The lock-in amplifier 1071 is electrically connected to the detection device 105, the chopper controller 1033 and the processing device 106, respectively. An output signal interface of the detection device 105 is connected to an input signal interface of the lock-in amplifier 1071. A frequency signal output interface of the chopper controller 1033 is connected to a reference signal interface of the lock-in amplifier 1071. The lock-in amplifier 1071 separates a specific carrier frequency signal according to a frequency of a reference signal.

As a preferred solution, the spectrometer 100 provided by the embodiment of the present disclosure further includes: signal amplifier 108. The signal amplifier 108 is made of a metamaterial with a surface including a series of engraved micro-nano structure arrays, and can amplify an optical signal of a specific wavelength. Specifically, in the present disclosure, the signal amplifier 108 amplifies an optical signal passing through the filter device 104 and having the preset wavelength, and an amplified optical signal is received by the detection device 105. In some technical solutions, the signal amplifier 108 can be omitted.

Figure 2:
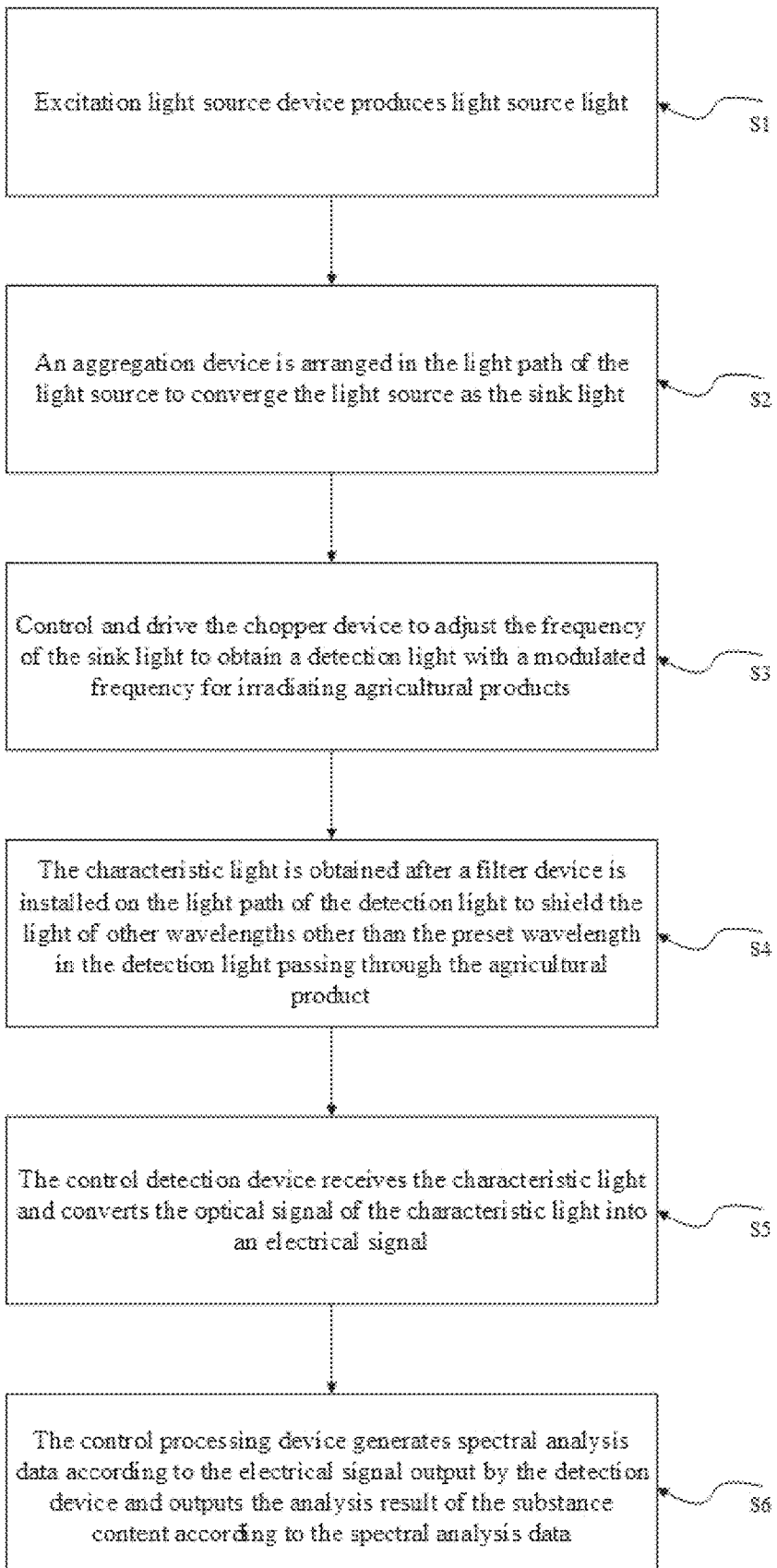

As shown in FIG. 2, as a preferred solution, an embodiment of the present disclosure provides a spectroscopic detection method. The method is realized by a spectrometer. The spectrometer includes: a light source device, a convergence device, a chopping device, a filter device, a detection device, and a processing device. The spectroscopic detection method mainly includes the following steps:

S1: The light source device 101 is activated to generate light.

S2: The convergence device 102 is provided on an optical path of the light generated by the light source device to obtain converged light.

S3: The chopping device 103 is controlled and driven to adjust a frequency of the converged light, thereby obtaining detection light used for irradiating an agricultural product and having a modulation frequency.

S4: The filter device is provided on an optical path of the detection light to shield light of a wavelength other than a preset wavelength in detection light passing through the agricultural product, thereby obtaining characteristic light.

S5: The detection device 105 is controlled to receive the characteristic light and convert an optical signal of the characteristic light into an electrical signal.

S6: The processing device 106 is controlled to generate spectroscopic analysis data according to the electrical signal outputted by the detection device 105 and output a substance content analysis result according to the spectroscopic analysis data.

Specifically, for a trace substance or a nutrient substance in the agricultural product, the preset wavelength of the filter device 104 ranges from 400 nm to 5,000 nm.

More specifically, in order to detect lycopene in the agricultural product, the preset wavelength of the filter device is defined as follows:

As a preferred solution, the preset wavelength of the filter device includes at least 900 nm to 1,200 nm.

As a preferred solution, the preset wavelength of the filter device includes at least 1,300 nm to 1,500 nm.

As a preferred solution, the preset wavelength of the filter device includes at least 1,600 nm to 1,800 nm.

As a preferred solution, the preset wavelength of the filter device includes at least 2,200 nm to 2,400 nm.

More preferably, the preset wavelength of the filter device includes at least one or more of 900 nm, 1,180 nm, 1,400 nm, 1,720 nm and 2,350 nm.

Figure 3:
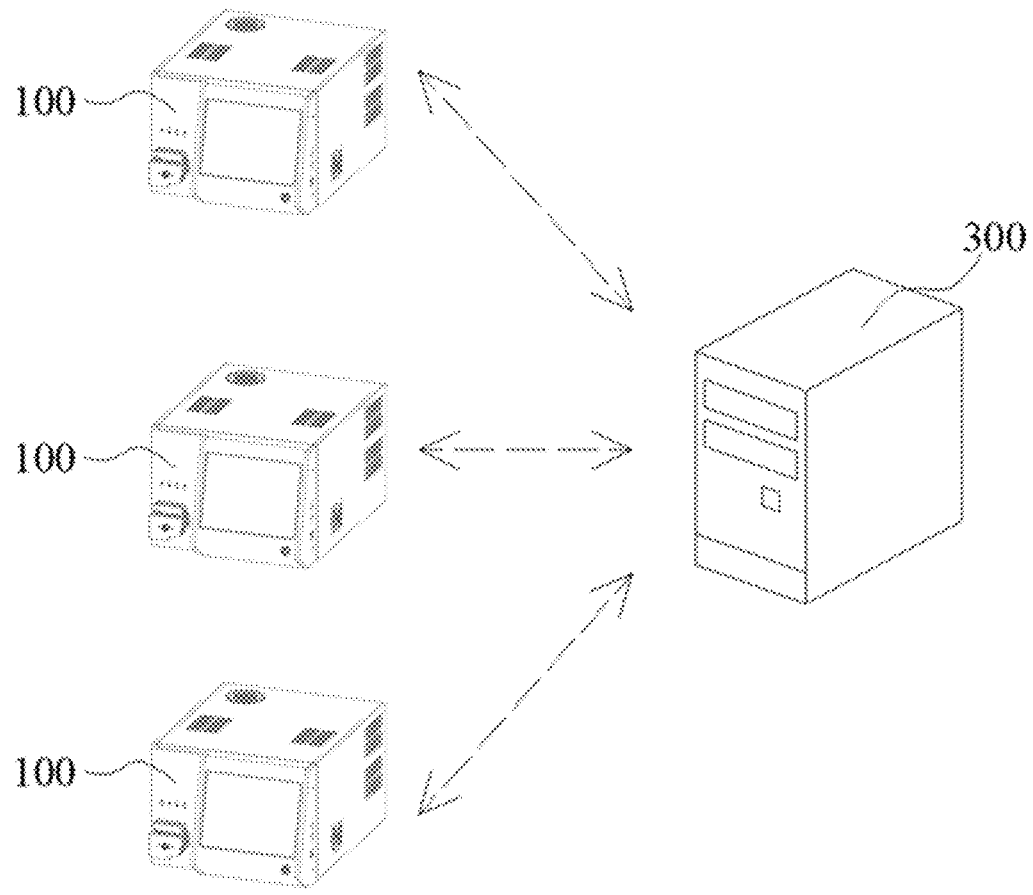

As shown in FIG. 3, as a preferred solution, an embodiment of the present disclosure provides a spectroscopic detection method. The method is realized by a plurality of spectrometers 100 and server 300.

As shown in FIG. 2, the spectroscopic detection method includes steps executed by each of the spectrometers:

S1: Light source device 101 is activated to generate light.

S2: Convergence device 102 is provided on an optical path of the light generated by the light source device to obtain converged light.

S3: Chopping device 103 is controlled and driven to adjust a frequency of the converged light, thereby obtaining detection light used for irradiating an agricultural product and having a modulation frequency.

S4: Filter device is provided on an optical path of the detection light to shield light of a wavelength other than a preset wavelength in detection light passing through the agricultural product, thereby obtaining characteristic light.

S5: Detection device 105 is controlled to receive the characteristic light and convert an optical signal of the characteristic light into an electrical signal.

S6: Processing device 106 is controlled to generate spectroscopic analysis data according to the electrical signal outputted by the detection device 105 and output a substance content analysis result according to the spectroscopic analysis data.

The preset wavelength of the filter device ranges from 400 nm to 5,000 nm.

As shown in FIG. 4, the spectroscopic detection method includes steps executed by the server 300:

St1: In response to the analysis result outputted by the processing device of one spectrometer, a modulation frequency and an analysis result in historical data of the spectrometer are queried.

St2: A modulation frequency and an analysis result corresponding to last N sets of data in the historical data are input to a modulation frequency analysis model, such that the modulation frequency analysis model outputs a modulation frequency predicted value and a corresponding confidence.

St3: Whether the confidence is greater than or equal to a preset confidence threshold is determined. If yes, the modulation frequency predicted value is used and fed back to the spectrometer. If no, the modulation frequency predicted value is not used.

Specifically, the modulation frequency analysis model is trained by taking modulation frequencies and analysis results in historical data of the plurality of spectrometers as training data.

Figure 5:
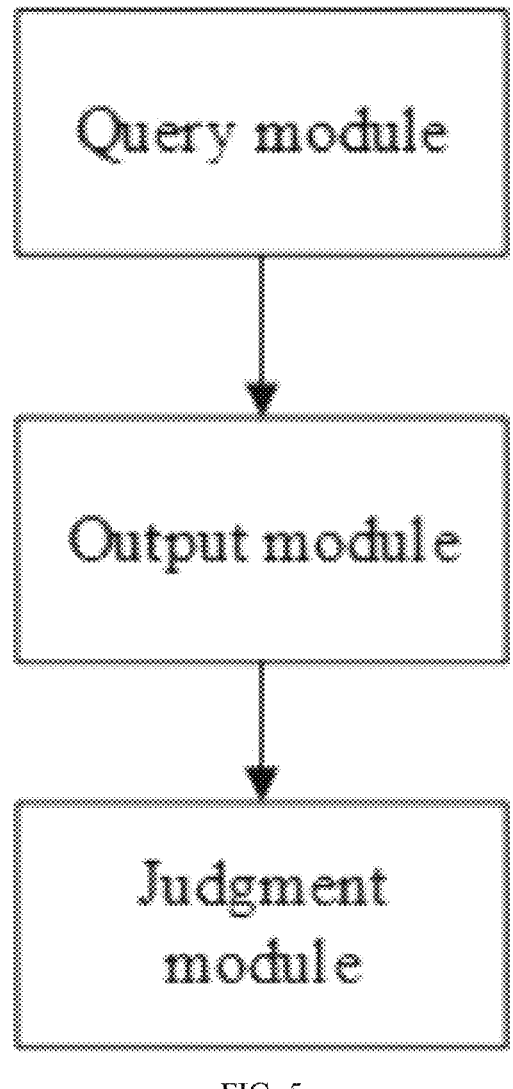

As shown in FIG. 5, a spectroscopic detection device provided by the present disclosure includes: a query module configured to query, in response to the analysis result outputted by the processing device of one spectrometer, a modulation frequency and an analysis result in historical data of the spectrometer; an output module configured to input a modulation frequency and an analysis result corresponding to last N sets of data in the historical data to a modulation frequency analysis model, such that the modulation frequency analysis model outputs a modulation frequency predicted value and a corresponding confidence; and a determination module configured to determine whether the confidence is greater than or equal to a preset confidence threshold, use the modulation frequency predicted value and feed the modulation frequency predicted value back to the spectrometer if yes, and not use the modulation frequency predicted value if no. The modulation frequency analysis model is trained by taking modulation frequencies and analysis results in historical data of the plurality of spectrometers as training data.

As a preferred solution, the N is a positive integer, and can be set and adjusted.

With the above solution, when applied to a fruit production line, the spectroscopic detection device can quickly select and adjust a spectral band according to different trace substances or nutrient substances to be detected in a batch of fruits. The system trained model can reduce a training cost and improve a prediction accuracy.

As a preferred solution, the modulation frequency analysis model is a convolutional neural network (CNN) model, and its input data are a plurality of matrices converted from a plurality of standard spectrograms and corresponding modulation frequencies. The modulation frequency analysis model is trained to realize a prediction function. The specific architecture and training method of the model are known to those skilled in the art, and are not repeated.

Figure 6:
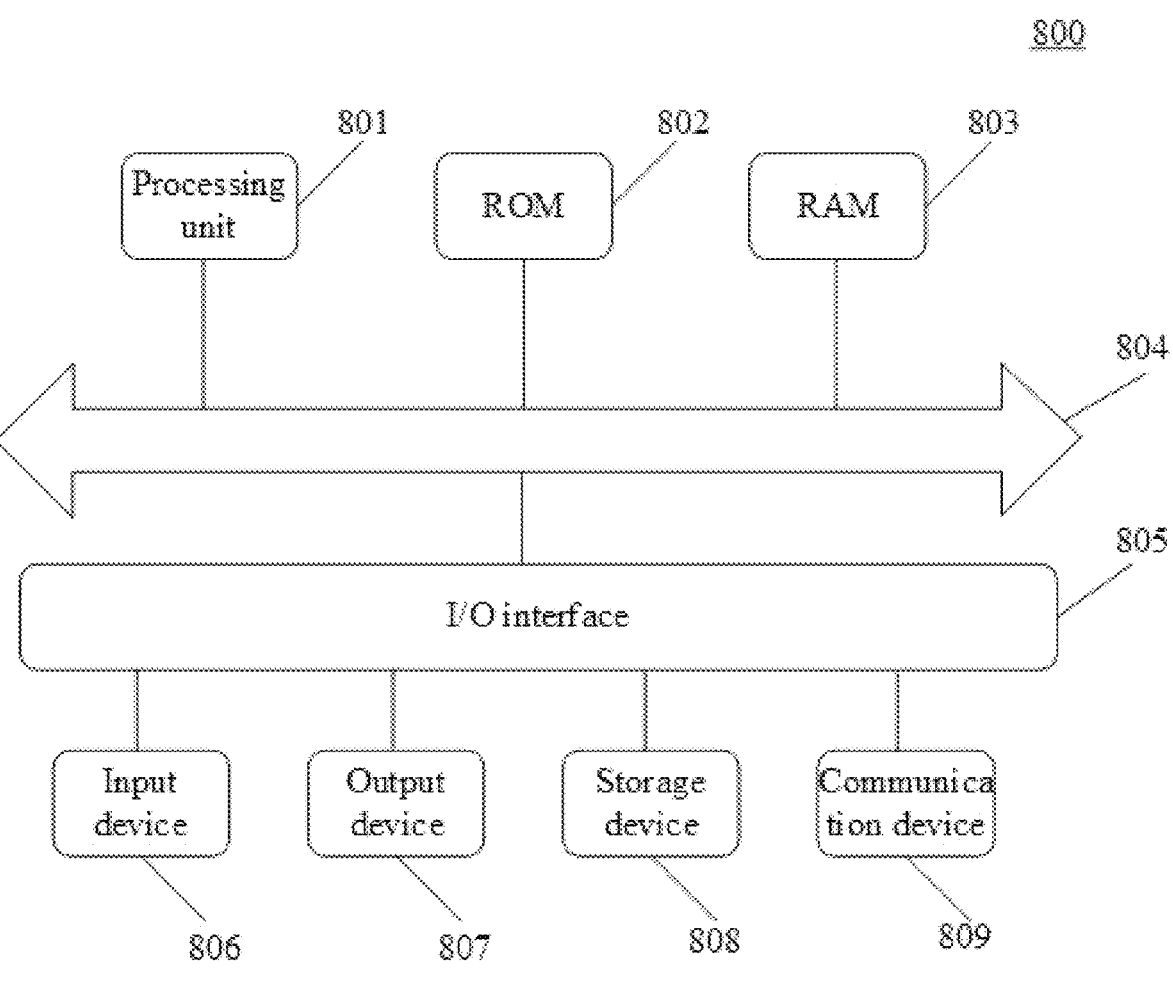

As shown in FIG. 6, electronic equipment 800 may include processing device (such as a central processing unit (CPU) and a graphics processing unit (GPU)) 801, which can perform various suitable actions and processing according to a program stored in read-only memory (ROM) 802 or a program loaded from storage device 808 to random access memory (RAM) 803. The RAM 803 may further store various programs and data required for operation of the electronic equipment 800. The processing device 801, the ROM 802, and the RAM 803 are mutually connected via bus 804. Input/output (I/O) interface 805 is also connected to the bus 804.

Usually, the following devices can be connected to the I/O interface 805: input device 806 including a touch screen, a touch tablet, a keyboard, a mouse, a camera, a microphone, an accelerometer, a gyroscope and the like; output device 807 including a liquid crystal display (LCD), a speaker, a vibrator and the like; the storage device 808 including a magnetic tape, a hard disk and the like; and communication device 809. The communication device 809 may allow the electronic equipment 800 to exchange data with other devices in wireless or wired communication. Although the electronic equipment 800 with various devices is shown in FIG. 6, it is to be understood that all shown devices are implemented or provided unnecessarily. Alternatively, more or less devices can be implemented or provided. In FIG. 6, each block may represent one device, and may also represent a plurality of devices as required.

Particularly, according to the embodiments of the present disclosure, the process described above with reference to the flowchart may be implemented as a computer software program. For example, an embodiment of the present disclosure includes a computer program product, including a computer program carried by a computer-readable medium. The computer program includes a program code for executing the method shown in the flowchart. In such an embodiment, the computer program may be downloaded and installed from the network through the communication device 809, installed from the storage device 808, or installed from the ROM 802. When the computer program is executed by the processing device 801, the functions defined by the methods in some embodiments of the present disclosure are executed.

It should be noted that the computer-readable medium in some embodiments of the present disclosure may be a computer-readable signal medium, a computer-readable storage medium, or a combination thereof. The computer-readable storage medium may be, for example, but not limited to, electrical, magnetic, optical, electromagnetic, infrared, or semiconductor systems, apparatuses, or devices, or any combination thereof. More specific examples of the computer-readable storage medium may include, but are not limited to: an electrical connection with one or more conducting wires, a portable computer disk, a hard disk, a RAM, a ROM, an erasable programmable ROM (an EPROM or a flash memory), an optical fiber, a portable compact disk read-only memory (CD-ROM), an optical storage device, a magnetic storage device, or any suitable combination thereof.

In some embodiments of the present disclosure, the computer-readable storage medium may be any tangible medium that contains or stores a program, and the program may be used by or in combination with an instruction execution system, apparatus, or device. In some embodiments of the present disclosure, the computer-readable signal medium may include a data signal propagated in a baseband or as a part of a carrier, and computer-readable program code is carried therein. The propagated data signal may be in various forms, including but not limited to an electromagnetic signal, an optical signal, or any suitable combination thereof. The computer-readable signal medium may alternatively be any computer-readable medium except the computer-readable storage medium. The computer-readable medium may send, propagate or transmit a program used by or used in combination with an instruction execution system, apparatus or device. The program code contained on the computer-readable medium may be transmitted using any suitable medium, including but not limited to: a wire, an optical fiber, a radio frequency (RF), or any suitable combination thereof.

In some implementations, a client and a server may communicate with any existing known or future researched network protocol such as a hypertext transfer protocol (HTTP), and can be connected to a digital data communication (such as a communication network) in any form or medium. Examples of the communication network include a local area network ("LAN"), a wide area network ("WAN"), an international network (such as an Internet), a peer-to-peer network (such as an adhoc peer-to-peer network), and any present known or future researched network.

The computer-readable medium may be contained in the above-described electronic equipment, or may exist alone without being assembled in the electronic equipment. The computer-readable medium stores one or more programs. When executed by the electronic equipment, the one or more programs allow the electronic equipment to: query, in response to the analysis result outputted by the processing device of one spectrometer, a modulation frequency and an analysis result in historical data of the spectrometer; input a modulation frequency and an analysis result corresponding to last N sets of data in the historical data to a modulation frequency analysis model, such that the modulation frequency analysis model outputs a modulation frequency predicted value and a corresponding confidence; and determine whether the confidence is greater than or equal to a preset confidence threshold is determined, use the modulation frequency predicted value and feed the modulation frequency predicted value back to the spectrometer if yes, and not use the modulation frequency predicted value if no. The modulation frequency analysis model is trained by taking modulation frequencies and analysis results in historical data of the plurality of spectrometers as training data.

The computer program code for executing the operations in some embodiments of the present disclosure may be compiled by using one or more program design languages or a combination thereof. The programming languages include object oriented programming languages, such as Java, Smalltalk, and C++, and conventional procedural programming languages, such as "C" or similar programming languages. The program code may be executed fully on a user computer, executed partially on a user computer, executed as an independent software package, executed partially on a user computer and partially on a remote computer, or executed fully on a remote computer or a server. In a circumstance in which a remote computer is involved, the remote computer may be connected to a user computer over any type of network, including a LAN or a WAN, or may be connected to an external computer (for example, connected over the Internet by using an Internet service provider).

The flowcharts and block diagrams in the accompanying drawings illustrate architectures, functions, and operations of possible implementations of the system, method, and computer program product according to various embodiments of the present disclosure. In this regard, each block in the flowcharts or block diagrams may represent a module, a program segment or a part of code, and the module, the program segment or the part of code includes one or more executable instructions for implementing specified logic functions.

It should also be noted that, in some alternative implementations, the functions marked in the blocks may alternatively occur in a different order from that marked in the drawings.

For example, two successively shown blocks actually may be executed in parallel substantially, or may be executed in reverse order sometimes, depending on the functions involved. It should also be noted that each block in the flowcharts and/or block diagrams and combinations of the blocks in the flowcharts and/or block diagrams may be implemented by a dedicated hardware-based system for executing specified functions or operations, or may be implemented by a combination of dedicated hardware and computer instructions.

The units described in some embodiments of the present disclosure may be implemented in a form of software or in a form of hardware. The described units may also be provided in a processor. Names of these units do not constitute a limit to the units in some cases.

The functions described above in this specification may be at least partially performed by one or more hardware logic units. For example, unrestrictively, exemplary hardware logic components that can be used include: a field programmable gate array (FPGA), an application-specific integrated circuit (ASIC), an application-specific standard part (ASSP), a system on chip (SOC), a complex programmable logic device (CPLD), and the like.

The above description is merely an illustration of preferred embodiments of the present disclosure and the technical principle in use. Those skilled in the art should understand that the inventive scope in the embodiments of the present disclosure is not limited to the technical solution formed by a specific combination of the foregoing technical features, but should cover other technical solutions formed by any combination of the foregoing technical features or equivalent features thereof without departing from the foregoing inventive concept, for example, a technical solution formed by replacing the foregoing feature with a technical feature having a similar function disclosed in (but not limited to) the embodiments of the present disclosure.

What is claimed is:

1. A spectrometer for detecting a trace element in an agricultural product, comprising:

a light source device configured to generate light required by spectroscopic detection;

a convergence device configured to converge the light generated by the light source device; and a chopping device configured to modulate a frequency of light converged by the convergence device;

a filter device configured to shield light of a wavelength other than a preset wavelength;

a detection device configured to receive light passing through a to-be-detected agricultural product and the filter device, and convert an optical signal into an electrical signal;

a processing device configured to generate spectroscopic analysis data according to the electrical signal outputted by the detection device and output a substance content analysis result according to the spectroscopic analysis data; and a signal amplifier configured to amplify an optical signal passing through the filter device and having the preset wavelength;

wherein the preset wavelength of the filter device ranges from 400 nm to 5,000 nm; and wherein the signal amplifier is made of a metamaterial having a micro-nano structure array.

2. The spectrometer for detecting the trace element in the agricultural product according to claim 1, wherein
the light generated by the light source device comprises infrared light.

3. The spectrometer for detecting the trace element in the agricultural product according to claim 1, wherein
a wavelength of the light generated by the light source device ranges from 400 nm to 5,000 nm.

4. The spectrometer for detecting the trace element in the agricultural product according to claim 1, wherein
the light source device comprises a halogen lamp.

5. The spectrometer for detecting the trace element in the agricultural product according to claim 1, wherein
the convergence device comprises a convex lens.

6. The spectrometer for detecting the trace element in the agricultural product according to claim 1, wherein
the chopping device comprises:
an optical chopper comprising a rotary vane with adjustable rotational frequency for periodically shielding the light converged by the convergence device;
a chopper driver configured to drive the rotary vane to rotate; and
a chopper controller configured to control operation of the chopper driver to control a rotational frequency of the rotary vane;
wherein the chopper driver is mechanically connected to the rotary vane of the optical chopper, and the chopper driver is electrically connected to the chopper controller.

7. The spectrometer for detecting the trace element in the agricultural product according to claim 6, further comprising:
a phase lock device configured to improve a signal-to-noise ratio (SNR) of the electrical signal outputted by the detection device to the processing device.

8. The spectrometer for detecting the trace element in the agricultural product according to claim 7, wherein
the phase lock device comprises a lock-in amplifier, and the lock-in amplifier is electrically connected to the detection device, the chopper controller and the processing device, respectively.

9. The spectrometer for detecting the trace element in the agricultural product according to claim 1, wherein
the detection device comprises a near-infrared photodetector; and the near-infrared photodetector comprises at least one of a Polycrystalline lead sulfide (PbS) detector array or an Indium Gallium Arsenide (InGaAs) detector array for detecting an optical signal of the preset wavelength.

10. A use method of the spectrometer for detecting the trace element in the agricultural product according to claim 1, comprising: using the spectrometer for detecting the trace element in the agricultural product to detect a lycopene content in the agricultural product.

11. The use method according to claim 10, wherein
in the spectrometer for detecting the trace element in the agricultural product, the light generated by the light source device comprises infrared light.

12. The use method according to claim 10, wherein
in the spectrometer for detecting the trace element in the agricultural product, a wavelength of the light generated by the light source device ranges from 400 nm to 5,000 nm.

13. The use method according to claim 10, wherein
in the spectrometer for detecting the trace element in the agricultural product, the light source device comprises a halogen lamp.

14. The use method according to claim 10, wherein
in the spectrometer for detecting the trace element in the agricultural product, the convergence device comprises a convex lens.

15. The use method according to claim 10, wherein
in the spectrometer for detecting the trace element in the agricultural product, the chopping device comprises:
an optical chopper comprising a rotary vane with adjustable rotational frequency for periodically shielding the light converged by the convergence device;
a chopper driver configured to drive the rotary vane to rotate; and
a chopper controller configured to control operation of the chopper driver to control a rotational frequency of the rotary vane;
wherein the chopper driver is mechanically connected to the rotary vane of the optical chopper, and the chopper driver is electrically connected to the chopper controller.

16. The use method according to claim 15, wherein
the spectrometer for detecting the trace element in the agricultural product further comprises:
a phase lock device configured to improve a signal-to-noise ratio (SNR) of the electrical signal outputted by the detection device to the processing device.

17. The use method according to claim 16, wherein
the phase lock device comprises a lock-in amplifier, and the lock-in amplifier is electrically connected to the detection device, the chopper controller and the processing device, respectively.

18. The use method according to claim 10, wherein
in the spectrometer for detecting the trace element in the agricultural product, the detection device comprises a near-infrared photodetector; and the near-infrared photodetector comprises at least one of a Polycrystalline lead sulfide (PbS) detector array or an Indium Gallium Arsenide (InGaAs) detector array for detecting an optical signal of the preset wavelength.

* * * * *